(12) United States Patent  (10) Patent No.: US 7,242,185 B1
Bailey, III  (45) Date of Patent: Jul. 10, 2007

(54) METHOD AND APPARATUS FOR MEASURING A CONDUCTIVE FILM AT THE EDGE OF A SUBSTRATE

(75) Inventor: Andrew D. Bailey, III, Pleasanton, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 11/096,012

(22) Filed: Mar. 30, 2005

(51) Int. Cl.
*G01B 7/06* (2006.01)
*G01R 33/12* (2006.01)

(52) U.S. Cl. .................................... 324/229
(58) Field of Classification Search ............... 324/229
See application file for complete search history.

(56) References Cited

U.S. PATENT DOCUMENTS 4,849,694 A   7/1989  Coates
6,788,050 B2*  9/2004 Gotkis ..................... 324/239

OTHER PUBLICATIONS

Dusharme, "New Trends in Eddy Current Testing," http://www.qualitydigest.com/dec05/articles/01_article.shtml, pp. 1-7.

Welsby et al., "True Position Measurement with Eddy Current Technology," Nov. 1997, http://www.sensormag.com/articles/1197/eddy1197/main.shtml, pp. 1-13.

Baumgartner, "FEM Simulation of the Electromagnetic Field in Eddy Current Proximity Sensors," SENSOR 99; Seonsoren, Messaufnehmer & Systeme,pp. 1-6.

Yang, Chen, "Inductive Eddy Current Sensors for Position/Displacement Measurement and Nanopositioning," http://www.chenyang-ism.com/ EddyCurrentDistance.htm, 3 pp.

* cited by examiner

*Primary Examiner*—Reena Aurora
(74) *Attorney, Agent, or Firm*—IP Strategy Group, PC

(57) ABSTRACT

A method of determining a thickness at a thickness position of a conductive film on a substrate with a center zone and an edge zone is disclosed. The method includes providing a set of thickness correlation curves at a set of sensor position radii from a center of the substrate to a position where a sensitivity of an eddy current sensor to the edge zone is greater than zero. The method also includes measuring a set of eddy current responses at a sensor position of the set of sensor position radii. The method further includes correlating the set of eddy current responses to the thickness at the thickness position.

20 Claims, 9 Drawing Sheets

METHOD AND APPARATUS FOR MEASURING A CONDUCTIVE FILM AT THE EDGE OF A SUBSTRATE

BACKGROUND OF THE INVENTION

The present invention relates in general to substrate manufacturing technologies and in particular to methods and apparatus for measuring a conductive film at the edge of a substrate.

In the processing of a substrate, e.g., a semiconductor wafer, MEMS device, or a glass panel such as one used in flat panel display manufacturing, plasma is often employed. As part of the processing of a substrate (chemical vapor deposition, plasma enhanced chemical vapor deposition, physical vapor deposition, etc.) for example, the substrate is divided into a plurality of dies, or rectangular areas, each of which will become an integrated circuit. The substrate is then processed in a series of steps in which materials are selectively removed (etching) and deposited (deposition) in order to form electrical components thereon. Conductive films, such as metals, are particularly important materials in substrate manufacturing. For example, in a manufacturing method, known as dual damascene, dielectric layers are electrically connected by a conductive plug filling a via hole. Generally, an opening is formed in a dielectric layer, usually lined with a TaN or TiN barrier, and then subsequently filled with other conductive material (e.g., aluminum, copper, tantalum, ruthenium, tungsten, platinum, etc.) that allows electrical contact between two sets of conductive patterns. This establishes electrical contact between two active regions on the substrate, such as a source/drain region. Excess conductive material on the surface of the dielectric layer is typically removed by chemical mechanical polishing (CMP). A blanket layer of silicon nitride or silicon carbide may then be deposited to cap the copper.

Subsequently, in order to insure that the process is within acceptable parameters, it is often important to determine the thickness of a conductive film at a particular point on the substrate. One method of measurement is the use eddy current sensors. Generally, eddy currents are currents that are induced in a conductive media by an alternating magnetic field.

In general, if a first alternating current is applied to a wire wrapped in a generally solenoidal shape (e.g., the wire in an eddy current sensor), a first alternating electromagnetic field forms in and around the solenoid extending beyond the ends of the solenoid a distance on the order of the diameter of the solenoid. If this first field is brought into proximity with a second conductor (e.g., a conductive film on the substrate) a second alternating electrical current will also flow in the second conductor, causing a second field that interacts with (e.g., adds vectorially to) the first field and resulting in a perturbation to the field around the probe. These perturbations in the probe's initial field may cause detectable changes in the probe's electrical characteristics including the probe's impedance and frequency response. Using an impedance-voltage converter, the impedance change can be converted into a voltage change for further signal processing and analysis.

Many techniques are available for producing a signal from these detected differences in eddy current probe characteristics. For example, in a first technique, the width of the frequency dependent power absorption of the probe/eddy current sensor system (sensor system) can be reported. Likewise, in a second technique, the change in the magnitudes of the real and/or imaginary parts of the probe impedance can be reported between the probe with no second conductor and with the second conductor. These measurements are generally made using passive or active circuitry to produce a range of voltages that can be bounded by the signal with no second conductor present and the signal with a second conductor causing maximal change in the signal. The exact shape, thickness and conductivity of the second conductor that causes the maximal change in the probe signal generally depends on the probe geometry, excitation frequency and the method adopted for measurement, but generally it is a thick (on the order of many times the diameter of the probe) conductive film placed as near to the probe as possible.

Depending on the application, conductive or magnetic elements can also be incorporated into the design of the sensor to modify the spatial extent and magnitude of the sensor field and hence spatial and electrical sensitivity to the second conductive layer. For optimum performance in film thickness detection applications, the eddy current sensor system should maximize system sensitivity to the conductive target film's thickness while minimizing the sensor system's sensitivity to all other effects and variables. In ideal planar films, simple models and formulas exist to relate film parameters which may be of interest as well as thickness (including sheet resistivity, bulk film resistivity, grain size, etc.).

In such sensor systems, often the magnitude of the measured perturbation can subsequently be correlated to the thickness of a conductive film on the substrate thus enabling the sensor system to be configured to report film thickness. The reason eddy currents are generally calibrated to other parameters rather than deriving film properties from first principles is that the general three dimensional temporal field problem with an unknown second body is an under defined problem. Unfortunately, if the situation is sufficiently defined to allow closed form solutions that are useful to derive a film quantity, the physical situation is so simplified as to be impractical for use in a lab. That is, a calibration curve may be empirically determined that correlates a particular sensor signal voltage to a specific conductive film thickness in a particular geometric configuration.

However, the response of sensor to the magnetic field (e.g., eddy current perturbations), and hence its accuracy, is generally also affected by the proximity of the sensor to the substrate. That is, as the exciting sensor field is of limited spatial extent and its magnitude decreases as the position increases from the sensor, the overall eddy current perturbations caused by a second conductor being measured also decrease as the second conductor is moved further from the sensor. Thus, typically an eddy current sensor is said to be sensitive to proximity as well as film thickness. Numerous sensor systems are designed to exclude this proximity based cause of sensor perturbations as it is confounding to the correlation with perturbations caused by the target film's thickness.

Referring now to FIG. 1A, a simplified diagram of an eddy current sensor is shown. Generally, changes in the sensor's coil impedance 102 are caused by varying the distance 104 between the sensor (coil) and substrate 106. Since the electrical parameters of target material resistivity and permeability may determine the magnitude of the measured sensor perturbation, the sensor system is generally calibrated for the target material.

Referring now to FIG. 1B, a more detailed diagram of a sensor or head of the eddy current sensor of FIG. 1A is shown. As previously described, sensor coil 102 generates a first alternating electromagnetic field 204 that when brought into proximity by a distance 104 with a second conductor on the substrate 106, a second alternating electromagnetic field 206 will also flow in the substrate that can be correlated to the thickness of a conductive film. In addition, the direction 104 refers to the effective measuring proximity of sensor coil 102 and is usually on the order of a few radii of the coil 102. In general, the larger the first alternating electromagnetic field 208, the greater the area that can be measured.

Referring now to FIG. 2, a simplified diagram of a substrate on a turntable with an eddy current sensor arm is shown. Although in this example, substrate 202 rotates in direction 208, as sensor swing arm 204 moves sensors 206 across the surface of substrate 202, other configurations which move the sensors relative to the substrate exist.

Eddy current measurements generally assume an infinite plane of conductive film. For example, one method of eddy current measurements is to consider an infinite plane of conductive film placed a certain proximity to a set of parallel eddy current sensors. Usually the desired sensor system reported output is the film thickness, where factors such as conductivity, connectivity, grain structure, etc. are assumed to be constant, or alternatively, to have a negligible effect on the raw measured eddy current signal.

However, common methods of eddy current measurement presume the lack of edge effects to create eddy current discontinuities. In practice, this assumption tends only to exists in the center area of the substrate (center zone), since a portion of dies on the substrate surface may be placed near the substrate edge (edge zone) where the eddy current discontinuity may exist.

As previously described, eddy current sensors generally depend on creating an oscillating magnetic field and detecting the changes caused by the presence or absence of conductive material within the region of oscillating (vacuum) fields. Since a common way to make a magnetic field is with a coil of current carrying wire, the size of the eddy current sensors' sensing region (transverse size) is generally on the order of the size of the coil or magnetic material sheathing which can modify the flux shape at the sensor tip. That is, the smaller the coil or magnetic sheathing at the tip, the more spatially restricted and hence the more spatially sensitive (and expensive) the eddy current sensor.

Subsequently, reducing the size of the coil would only reduce the discontinuity effect of the substrate edge, and not eliminate it. Additional problems with sensor system repeatability and complexity may plague a solution attempting to reduce the edge effect by reducing the spatial size of the eddy current inducing field region. This can be understood because essentially the same magnitude of field is required to induce detectable perturbations in the coil due to film properties as in a large sensor, the gradient of the eddy current inducing field strength is much larger near a small coil than near a comparably film sensitive larger sensor.

One solution may be matrix deconvolution in which the measured spatial sensitivity of the sensor is expressed as a matrix. That is, the total sensor signal is generally expressed as a summation of the sensor's sub-local spatial sensitivities times and the as yet unknown film at the sub-local location. Given that the sensor sensitivities can be measured, by measuring at many points a matrix problem for the unknown film thicknesses can be determined. However, this method tends to be sensitive to the data input. Subsequently, many more measurements may be required to achieve a sufficient level of accuracy, substantially slowing down the measuring process.

Another solution may be the use thin conductive film measurement tools with reasonably small spatial resolution with either less smaller edge effects or of sufficient spatial restriction that the effects are not of interest for the measurement application. For example, the use of four point probes with about a 3 mm resolution and reasonably well understood edge compensation models, or the use of laser based surface acoustic wave detection less than 1 mm, etc. However, although thin conductive film measurement tools may measure various convolutions of quantities (i.e., conductive film conductivity, conductive film thickness, crystalline structure, film stack, sensor geometry, contact resistance, etc.), the raw data from the measurements must generally be processed at a later time in order to determine conductive film thickness.

In view of the foregoing, there are methods and apparatus for measuring a conductive film at the edge of a substrate.

SUMMARY OF THE INVENTION

The invention relates, in one embodiment, to a method of determining a thickness at a thickness position of a conductive film on a substrate with a center zone and an edge zone. The method includes providing a set of thickness correlation curves at a set of sensor position radii from a center of the substrate to a position where a sensitivity of an eddy current sensor to the edge zone is greater than zero. The method also includes measuring a set of eddy current responses at a sensor position of the set of sensor position radii. The method further includes correlating the set of eddy current responses to the thickness at the thickness position.

The invention relates, in another embodiment, to an apparatus for determining a thickness at a thickness position of a conductive film on a substrate with a center zone and an edge zone. The apparatus includes means for providing a set of thickness correlation curves at a set of sensor position radii from a center of the substrate to a position where a sensitivity of an eddy current sensor to the edge zone is greater than zero. The apparatus also includes means for measuring a set of eddy current responses at a sensor position of the set of sensor position radii. The apparatus further includes means for correlating the set of eddy current responses to the thickness at the thickness position.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

Figure 7:
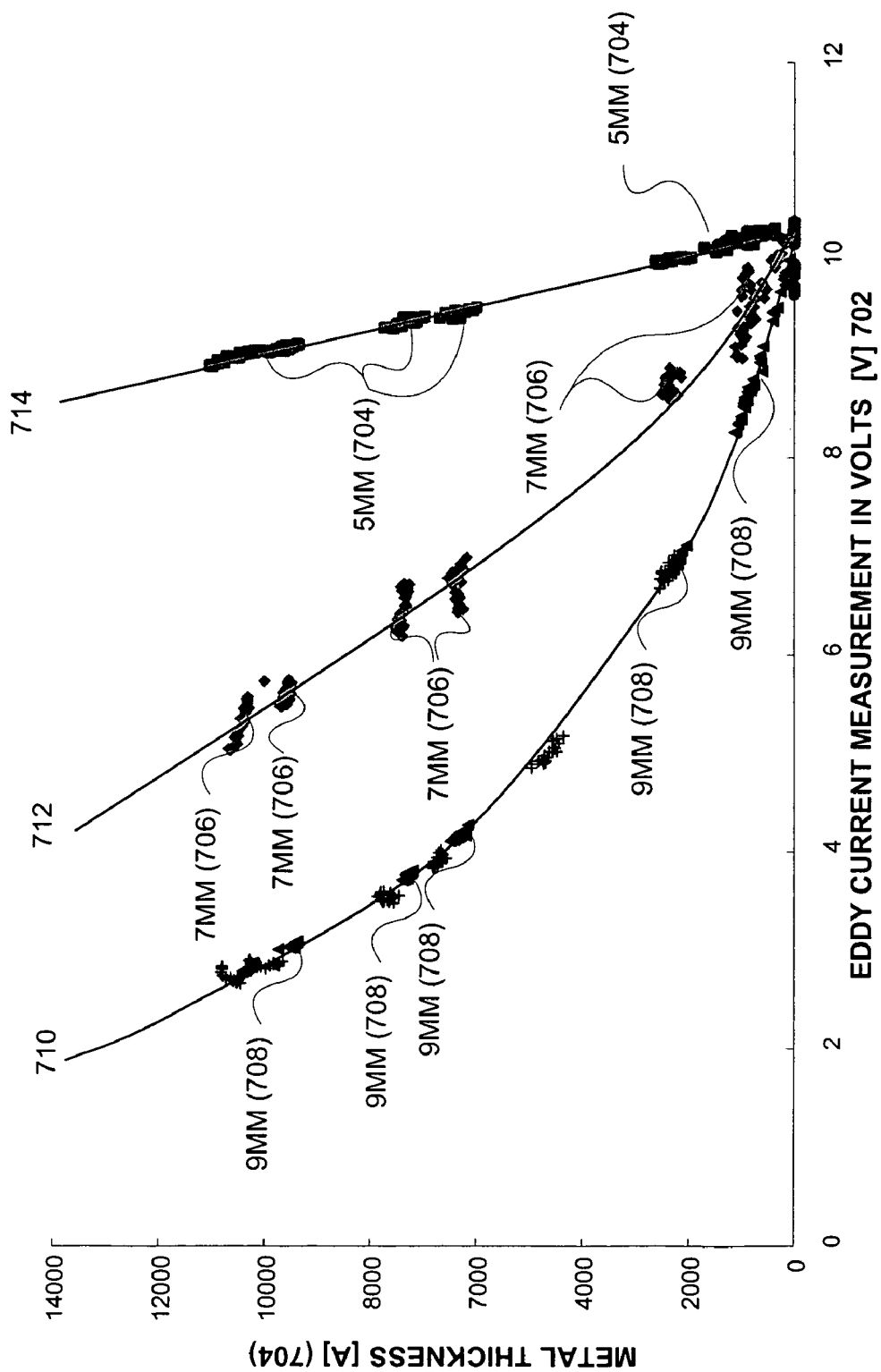
Figure 8:
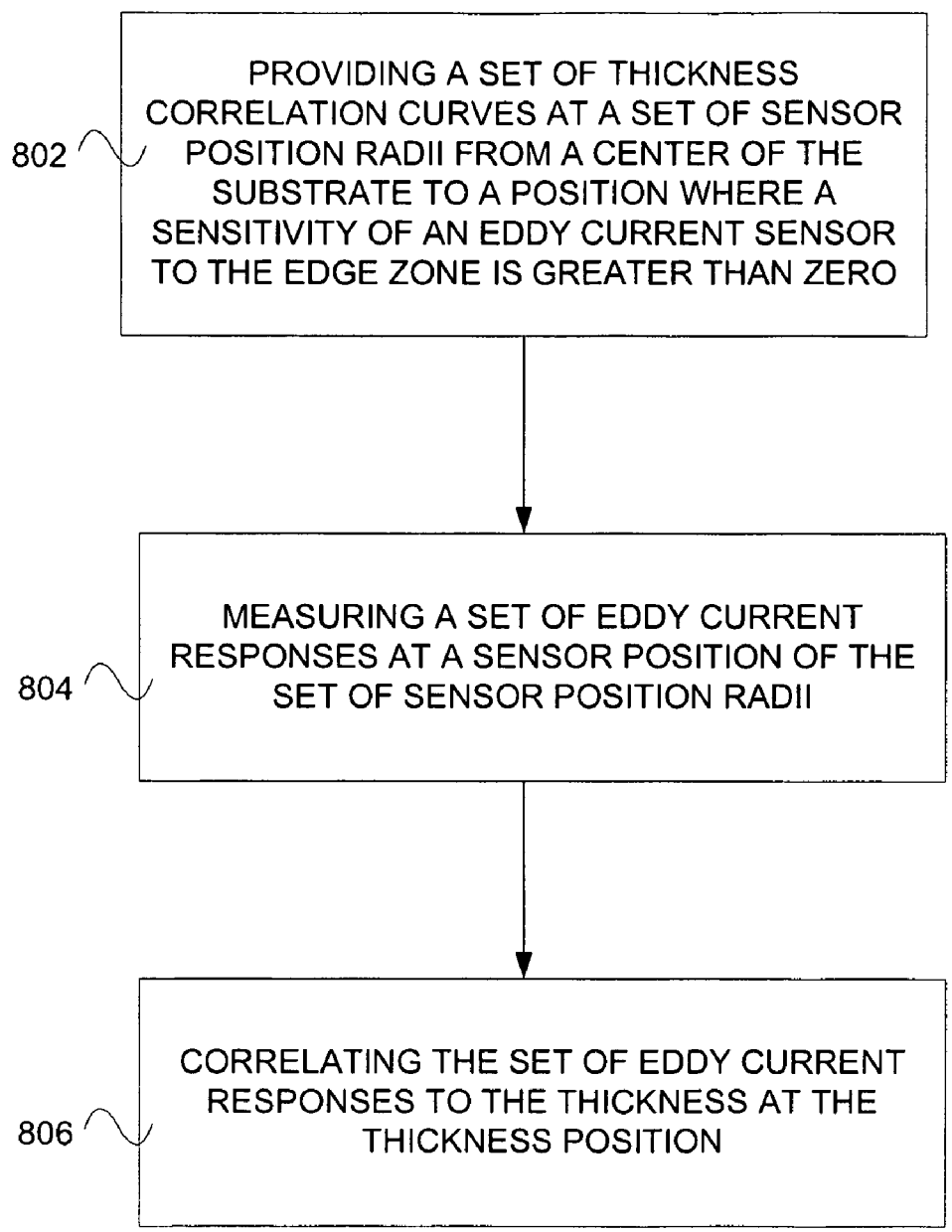

FIG. 7 illustrates a simplified diagram of a set of eddy current measurements from five sensors across a set of 200 mm substrates, with three calibration curves, according to one embodiment of the invention; and, FIG. 8 illustrates a simplified set of steps for determining a thickness at a thickness position of a conductive film on a substrate with a center zone and an edge zone.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

While not wishing to be bound by theory, it is believed by the inventor herein that a set of calibration curves can be separately determined for measuring conductive film thickness at a thickness position at the edge of the substrate. As previously described, a calibration curve may be empirically determined that correlates a voltage at a sensor position to a conductive film thickness at a thickness position on a substrate. However, common methods of eddy current measurement do not generally account for eddy current discontinuities at the substrate edge.

The sensitivity to the film of a sensor centered at the edge of the substrate is generally reduced from the ideal infinite plane condition, since the film does not extend beyond the substrate edge. In a non-obvious way, an eddy current sensor may be positioned off the substrate (offset) at a location in which a first alternating electromagnetic field generated by the sensor coil may still interact with the conductive film on the edge of the substrate to produce a second alternating electromagnetic field that may subsequently be measured. In general, by isolating the eddy current sensor off the substrate, only the edge portion (edge zone) of the conductive film is measured on the substrate, since film present in the center of the substrate (center zone) may have substantially less influence on the second alternating electromagnetic field. The distance between a sensor position and the corresponding thickness position on the substrate is generally called an offset distance.

In addition, since the presumed condition of an infinite plane of conductive film is generally not present on the substrate edge, a different set of calibration curves may be needed. In general, depending on the desired zone of interest on the substrate (i.e., center, edge, etc.) the appropriate calibration curve is used. Calibration curves are generally created empirically. That is, initially a set of eddy current measurements are generally taken for a set of locations on a plurality of substrates (e.g., a set of sensor positions at various sensor position radii). Independent thickness measurements are then made for the corresponding set of thickness positions in order to correlate a measured eddy current response to a conductive film thickness on a particular location on the substrate (e.g., thickness position). The independent measurements are generally made with four point probes, laser acoustic methods, cross section scanning electron microscope (SEM), transmission electron microscope (TEM), or other conventional methods. For example, in a common technique, a portion of the substrate is cleaved or removed, and then subsequently analyzed.

In an embodiment, the probe sensitivities are spatially dependent. In an embodiment, the probe sensitivities are sensitive to moving magnetic elements. In an embodiment, the probe sensitivities are sensitive to variable drive currents. In an embodiment, a difference between a first radius and a second radius of a set of sensor position radii is between about 1/10 to about 1/2 of a transverse size of the eddy current sensor. In an embodiment, a set of thickness correlation curves is created from a plurality of sensor position radii from a center of the substrate to a position off the substrate.

Figure 1A:
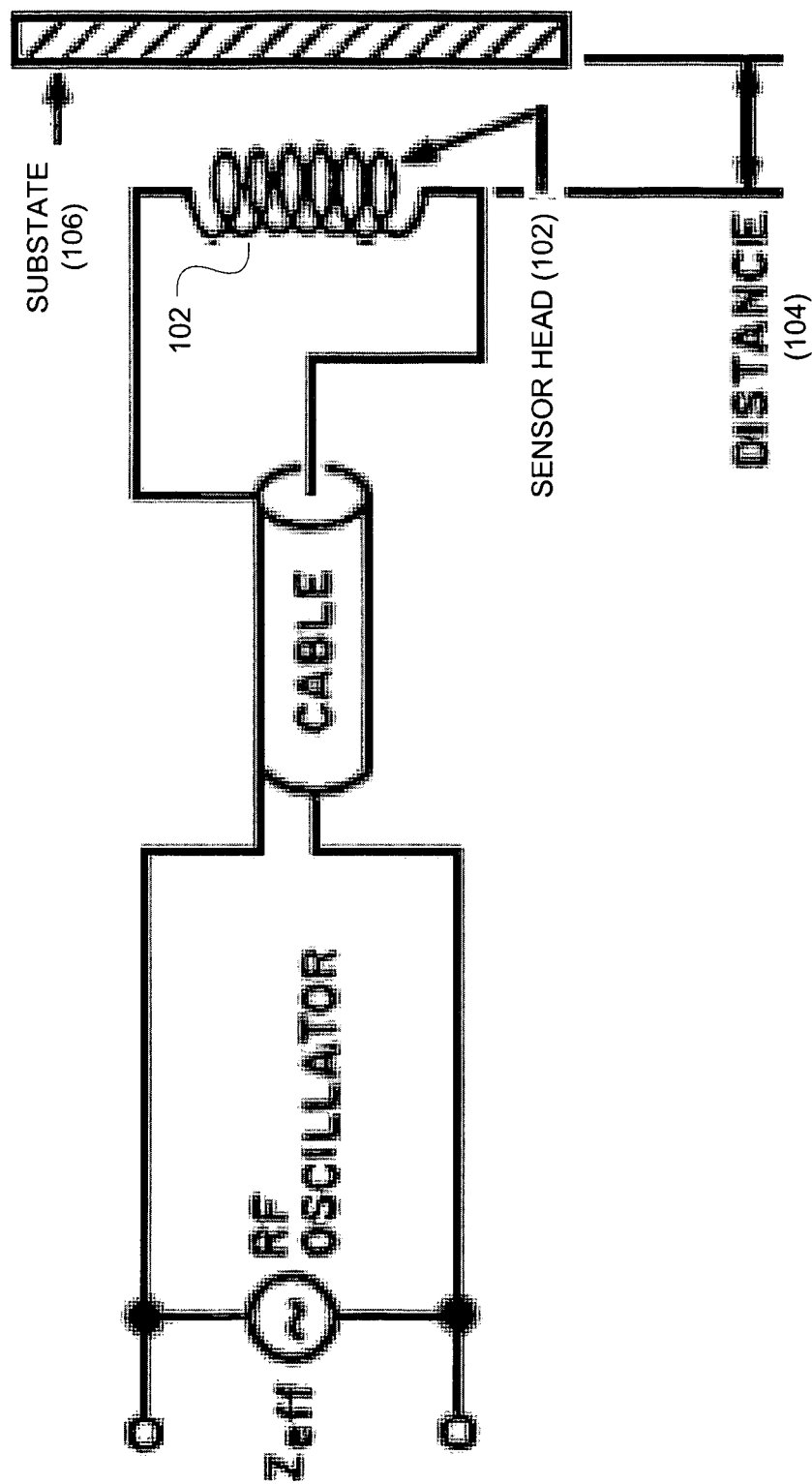
FIG. 1A illustrates a simplified diagram of an eddy current sensor.
Figure 1B:
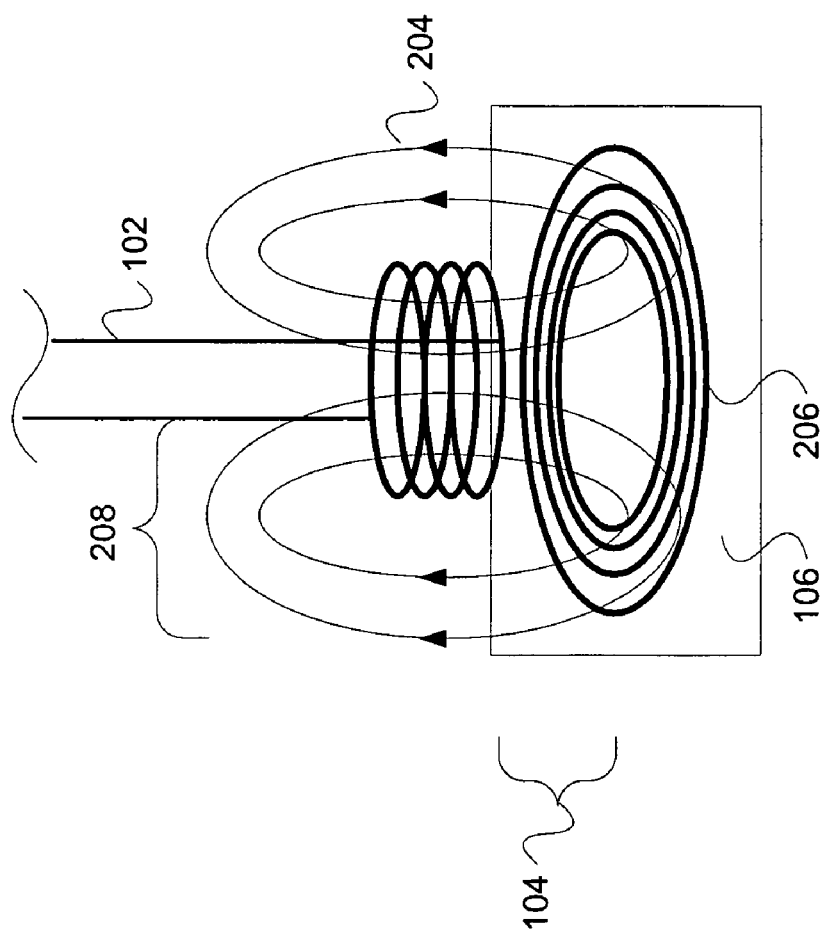
FIG. 1B illustrates a simplified diagram of the sensor hear of the eddy current sensor of FIG. 1A.
Figure 2:
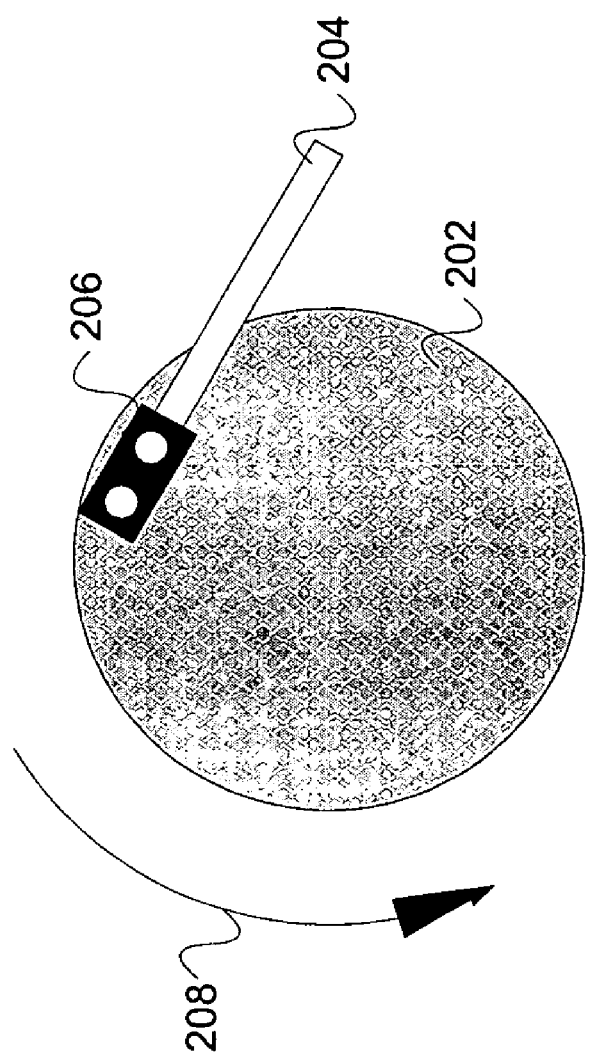
FIG. 2 illustrates a simplified diagram of a substrate on a turntable with a sensor arm.
Figure 3:
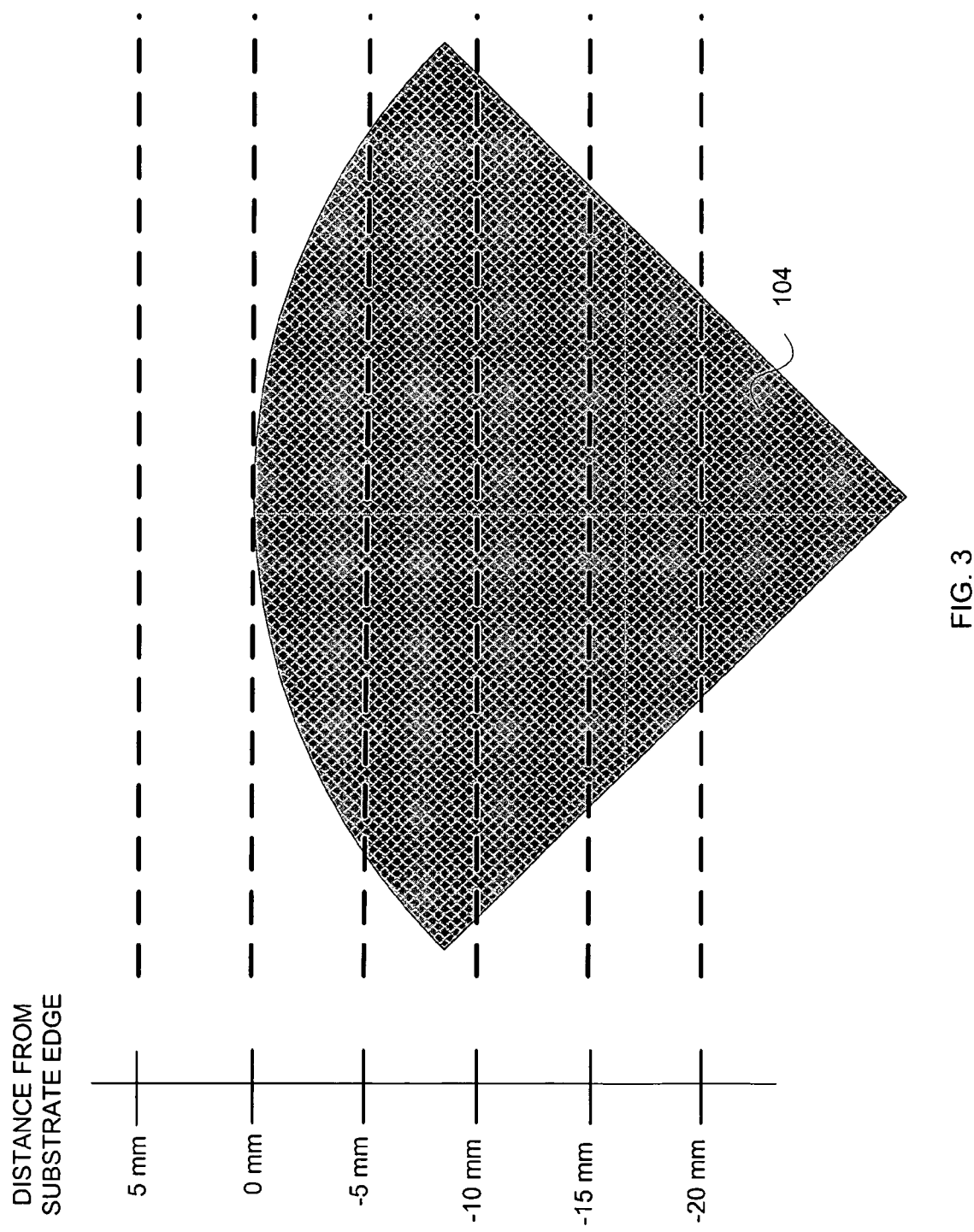
FIG. 3 illustrates a simplified diagram of a portion of the edge of a substrate.

Referring now to FIG. 3, a simplified diagram of a portion of a substrate is shown. In general, distance is measured from the edge of the substrate, in which a positive value is off the substrate, and a negative value is on the substrate toward the center. For example, 0 mm is the edge of the substrate, 5 mm is off the substrate, and −5 mm is on the substrate.

Figure 4:
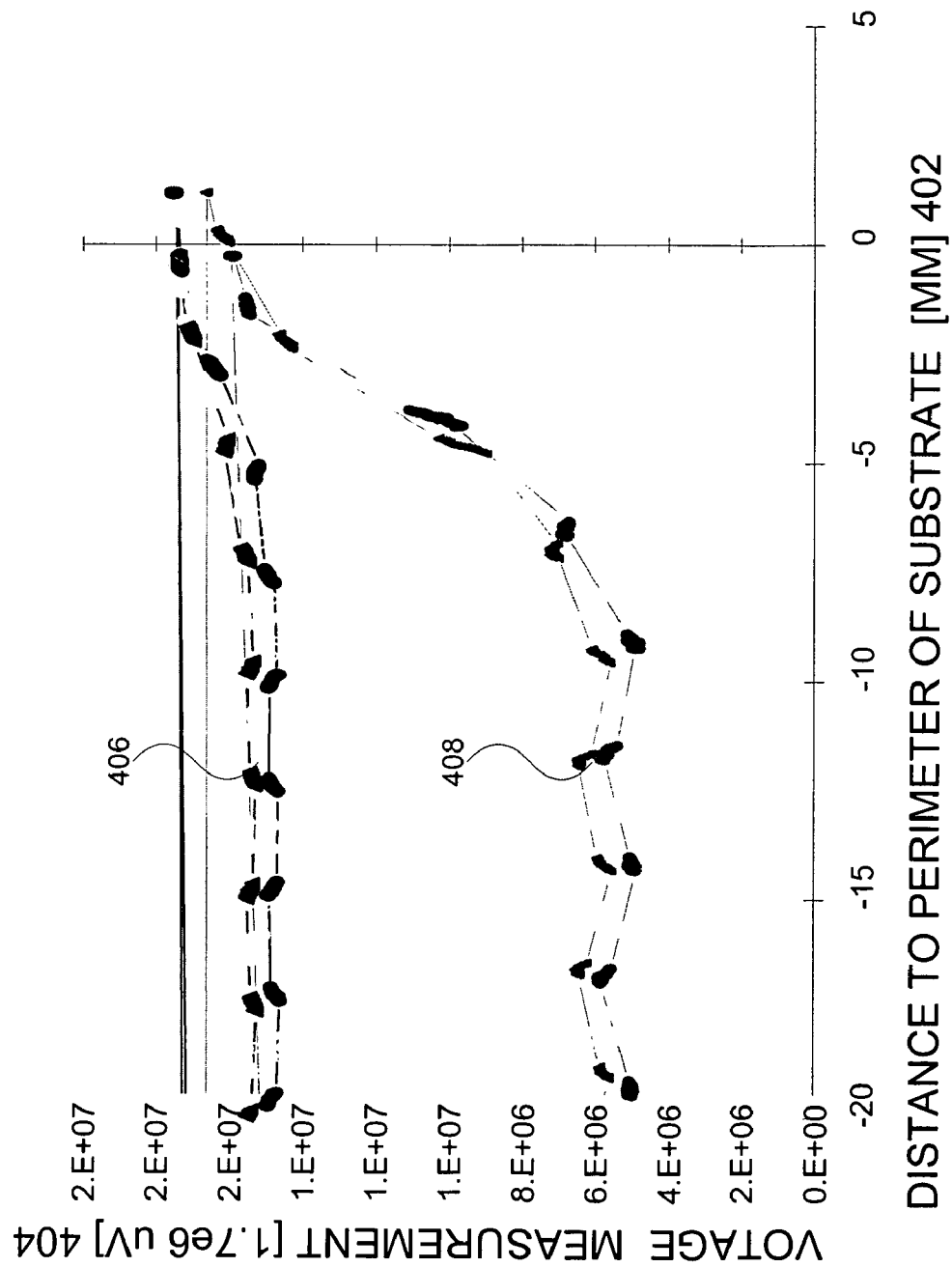
FIG. 4 illustrates a simplified diagram of a set of eddy current measurements on a substrate.

Referring now to FIG. 4, simplified diagram of a set of eddy current measurements on a substrate, as described in FIG. 3, is shown. These measurements were taken with a pair of probes (each with a ~7 mm radius of sensitivity) from a position off the substrate to a position on the substrate at two different angular positions. In a first angular position, only the slightly conductive substrate was present on the substrate, while in a second angular position, a thin film of Cu had been deposited with approximately a 3 mm edge exclusion. Horizontal axis 402 represents distance to the perimeter of the substrate, while vertical axis 404 represents voltage measurement in uV. Plot 406 represents eddy current measurements of Si (e.g., nearly non-conductive), while plot 408 represents eddy current measurements of Cu (e.g., conductive). As can be seen, as the probe moves from a position off the substrate at 5 mm, pass 0 mm, and toward −5 mm, the eddy current measurement substantially drops for Cu plot 408. This is generally caused by the creation of a second alternating electromagnetic field generated by the Cu metal film that is being measured by the eddy current sensor head. However, since the drop from about 2.E+07 at 0 mm to about 6.E+06 at −10 may be substantial, it is difficult to create a correlation curve suitable for both this region and that the region beyond −10 mm toward the center of the substrate. Si plot 406 is substantially stable since it generally does not create eddy currents for the eddy current sensor to measure. In general, a correlation curve can be visually created from eddy current plotted data (e.g., "eyeballed") or with standard mathematical minimization routines (i.e., linear regression, multiple regression, root mean square, etc.).

Figure 5:
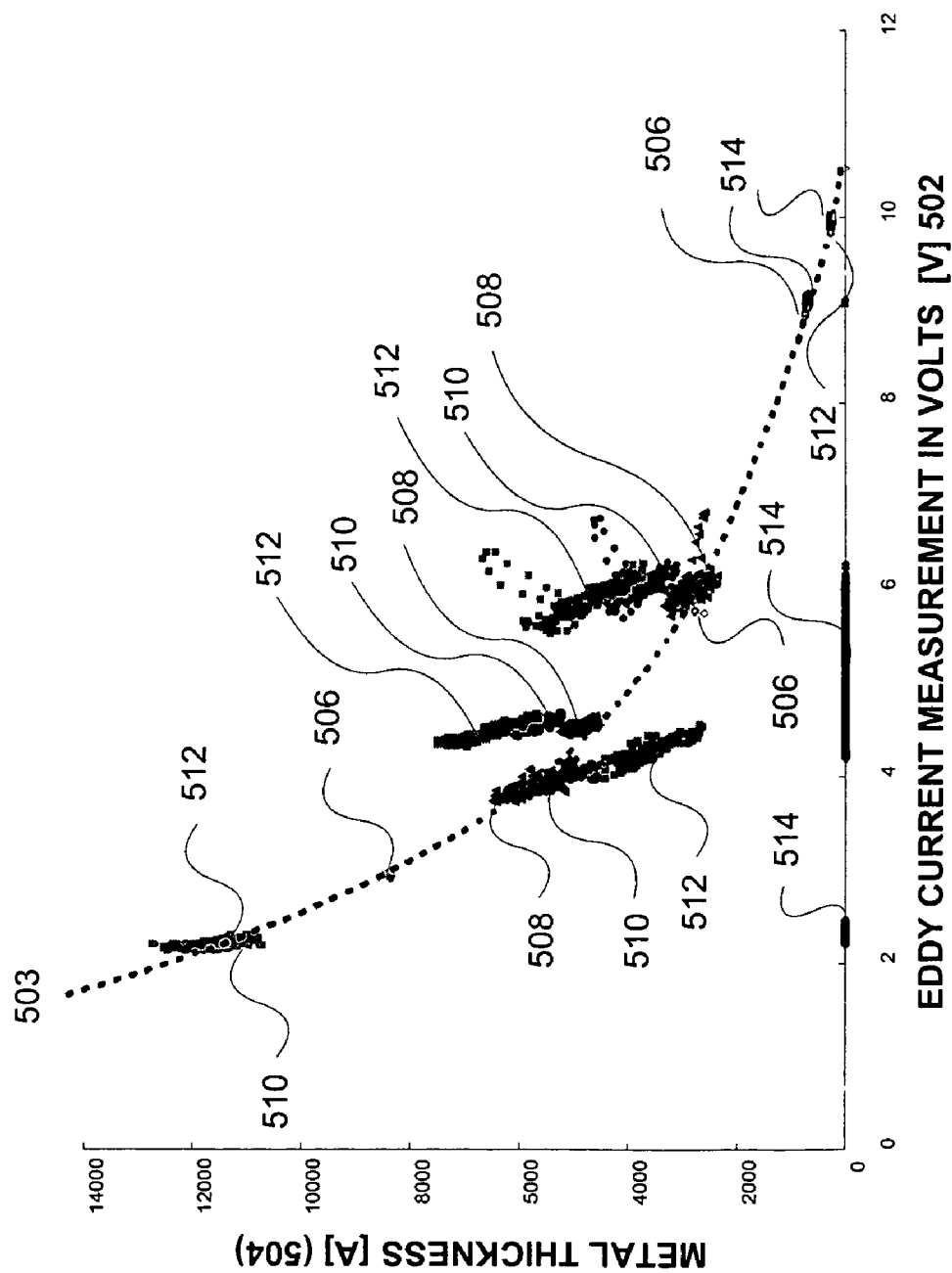
FIG. 5 illustrates a simplified diagram of a set of eddy current measurements from five sensors across a set of 300 mm substrates, and the resulting calibration curve.

Referring now to FIG. 5, a simplified diagram of a set of eddy current sensor measurements from five probes across a set of 300 mm substrates, and the resulting calibration curve, is shown. A series of substrates with different thicknesses of Cu were measured with a probe positioned centrally above a number of points located at different distances from the edge of the substrate. Substrates with different edge film thickness variations were included (i.e., film thickness increasing at the edge or decreasing at the edge). Horizontal axis 502 represents eddy current measurements in volts 502, while vertical axis 504 represents conductive film thickness in angstroms. In general, calibration curve 503 represents the best fit of all the collected data.

Eddy current sensor measurements set 1 506 was taken with the probe centered on positions greater than 15 mm from the edge of the substrate or closer to the center than −15 mm from the edge of the substrate as shown in FIG. 3. Eddy current sensor measurements set 2 508 was taken with the probe centered on positions 141 mm from the center of the substrate or −9 mm from the edge of the substrate as shown in FIG. 3. Eddy current sensor measurements set 3 508 was taken with the probe centered on positions 143 mm from the center of the substrate or −7 mm from the edge of the substrate as shown in FIG. 3. Eddy current sensor measurements set 4 512 was taken with the probe centered on positions 145 mm from the center of the substrate or −5 mm from the edge of the substrate as shown in FIG. 3. Eddy current sensor measurements set 5 514 was taken with the probe centered on positions 147 mm from the center of the substrate or −3 mm from the edge of the substrate as shown in FIG. 3.

As can be seen, eddy current sensor measurements set 1 506, positioned away from the edge of the substrate, is substantially isolated from edge effects, and so its measurements are generally on calibration curve 503. However, the remaining eddy current sensor measurements sets 2–5 are not as well correlated with calibration curve 503, since they are located near the edge of the substrate, and are subsequently influenced by edge effects. Overall, the fit of the measured data to calibration curve 503 is generally poor. That is, its calibration curve is not very predictive of the actual conductive film thickness at the edge of the substrate.

Figure 6:
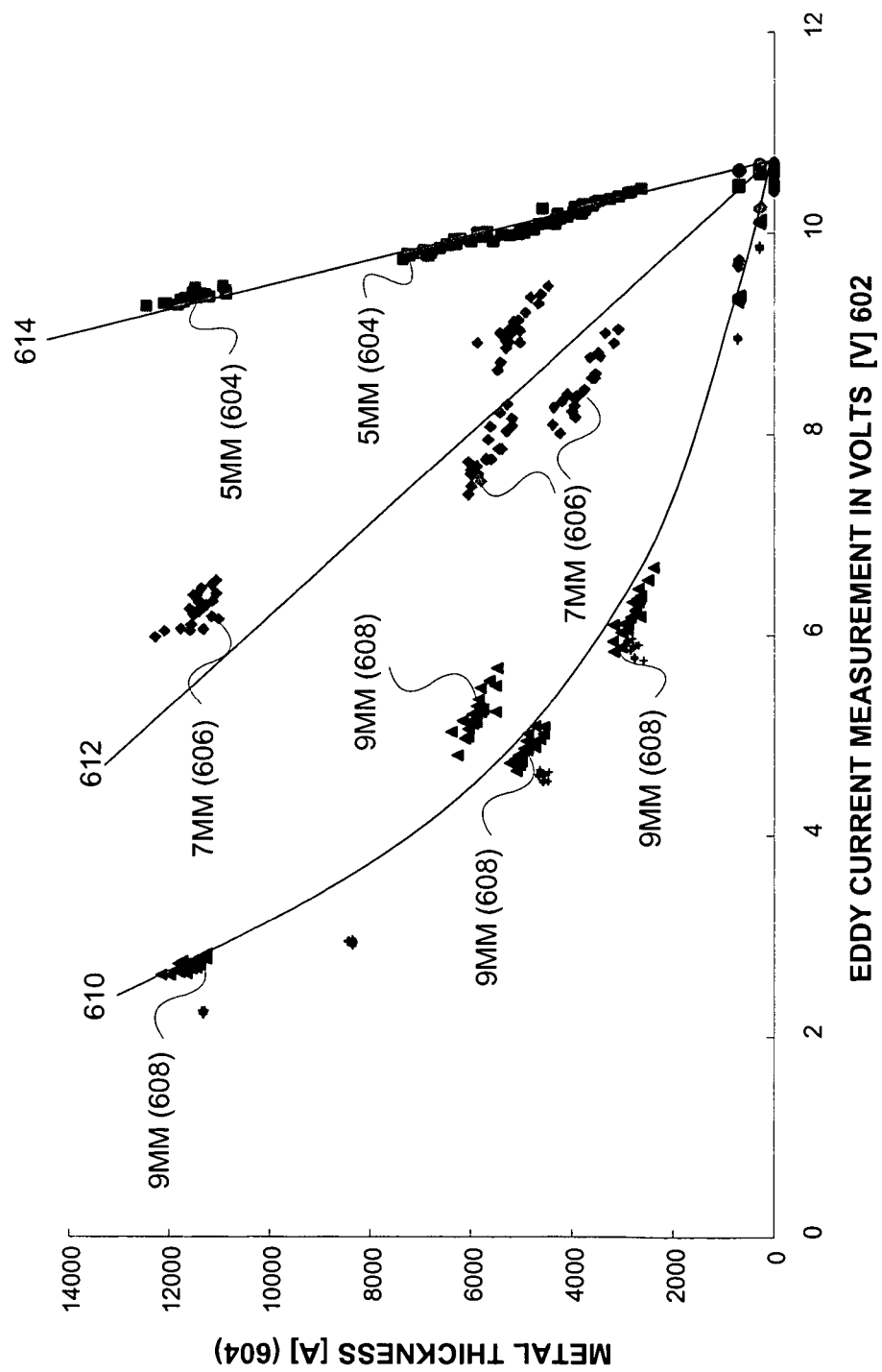
FIG. 6 illustrates a simplified diagram of a set of eddy current measurements from five sensors across a set of 300 mm substrates, with three calibration curves, according to one embodiment of the invention.

Referring now to FIG. 6, a simplified diagram of a set of eddy current measurements from the same substrates in FIG. 5 from five probe locations across a set of 300 mm substrates, with three calibration curves, according to one embodiment of the invention. Horizontal axis 602 represents eddy current measurements in volts, while vertical axis 604 represents conductive film thickness in angstroms.

Eddy current sensor measurement set 1 608 was taken with the probe centered on positions 141 mm from the center of the substrate or −9 mm from the edge of the substrate as shown in FIG. 3 (i.e., correlated with independent film thickness in the normal way.) Eddy current sensor measurements set 2 606 was taken with the sensor centered on positions 146 mm from the center of the substrate or −4 mm from the edge of the substrate as shown in FIG. 3 and correlated with the independent film thickness values for measurement points centered 143 mm from the center of the substrate or −7 mm from the edge of the substrate as shown in FIG. 3. Eddy current sensor measurements set 3 604 was taken with the probe centered on positions 150 mm from the center of the substrate or 0 mm from the edge of the substrate as shown in FIG. 3 and correlated with the independent film thickness values for measurement points centered 145 mm from the center of the substrate or −5 mm from the edge of the substrate as shown in FIG. 3. Points for eddy current measurements correlated with 147 mm from the center of the substrate are not shown for clarity.

As can be seen, unlike the prior art, a separate calibration curve can be generated for each sensor position. That is, eddy current sensor measurement set 1 608 generally correlates to calibration curve 610. Eddy current sensor measurement set 2 606 generally correlates to calibration curve 612. Eddy current sensor measurement set 3 604 generally correlates to calibration curve 612. Overall, each calibration curve may be substantially predictive of the actual conductive thickness at the edge of the substrate. In addition, the same methodology may work with the measurement sets taken with separate probes.

Referring now to FIG. 7, a simplified diagram of a set of eddy current measurements from five sensors across a set of 200 mm substrates, with three calibration curves, according to one embodiment of the invention. Horizontal axis 702 represents eddy current measurements in volts, while vertical axis 704 represents conductive film thickness in angstroms.

Eddy current sensor measurements set 1 708 was taken with the sensor centered on positions 141 mm from the center of the substrate or −9 mm from the edge of the substrate as shown in FIG. 3 (i.e., correlated with independent film thickness in the normal way). Eddy current sensor measurements set 2 706 was taken with the probe centered on positions 146 mm from the center of the substrate or −4 mm from the edge of the substrate as shown in FIG. 3 and correlated with the independent film thickness values for measurement points centered 143 mm from the center of the substrate or −7 mm from the edge of the substrate as shown in FIG. 3. Eddy current sensor measurements set 3 704 was taken with the probe centered on positions 150 mm from the center of the substrate or 0 mm from the edge of the substrate as shown in FIG. 3 and correlated with the independent film thickness values for measurement points centered 145 mm from the center of the substrate or −5 mm from the edge of the substrate as shown in FIG. 3. Points for eddy current measurements correlated with 147 mm from the center of the substrate are not shown for clarity.

As can be seen, again, unlike the prior art, a separate calibration curve can be generated for each probe position. That is, eddy current sensor measurements set 1 708 generally correlates to calibration curve 710. Eddy current sensor measurements set 2 706 generally correlates to calibration curve 712. Eddy current sensor measurements set 3 704 generally correlates to calibration curve 714. As before, each calibration curve is substantially predictive of the actual conductive thickness at the edge of the substrate.

Referring now to FIG. 8, a simplified set of steps for determining a thickness at a thickness position of a conductive film on a substrate with a center zone and an edge zone, according to one embodiment of the invention. Initially, in step 802, a set of thickness correlation curves is provided at a set of sensor position radii from a center of the substrate to a position where a sensitivity of an eddy current sensor to the edge zone is greater than zero. Next, a set of eddy current responses is measured at a sensor position of the set of sensor position radii, at step 804. Finally, the set of eddy current responses to the thickness at the thickness position is correlated, at step 806.

In an embodiment, a set of calibration curves may be created with a mathematical optimization function. In an embodiment, the mathematical optimization function is an arc tangent function. In general, it may be reasonable to assume that the eddy current transition off the substrate, where there is no conductive film, to on the substrate, where there is a normal amount of conductive film, will have a general plot shape, such as a suitably scaled arc tangent of the distance from the edge. Actual eddy current measurement data may then be normalized with respect to measured difference of the 'on substrate ' thickness of the conductive film and the 'off substrate measurement', and subsequently compared to the general plot. If a measurement is higher than the calculated transition plot, more conductive film may be present than normal, if lower, less may be present. Calibration of the deconvolved difference from normal may be performed and thus produce reported thicknesses with greater accuracy on the edge of the wafer.

While this invention has been described in terms of several preferred embodiments, there are alterations, permutations, and equivalents which fall within the scope of this invention. It should also be noted that there are many alternative ways of implementing the methods of the present invention.

Advantages of the invention include methods and apparatus for measuring a conductive film at the edge of a substrate. Additional advantages include the use of simple inexpensive eddy current sensors, the reduction of required measurements to accurately measure film thickness.

Having disclosed exemplary embodiments and the best mode, modifications and variations may be made to the disclosed embodiments while remaining within the subject and spirit of the invention as defined by the following claims.

What is claimed is:

1. A method of determining a thickness at a thickness position of a conductive film on a substrate, the method comprising:
   measuring a set of eddy current response values at a plurality of sensor position radii on a set of calibration conductive films on a set of calibration substrates;
   measuring, using one or more processes that are independent of eddy current measurement, a set of thickness values at a plurality of measurement points for said set of calibration conductive films on said set of calibration substrates;
   correlating said set of eddy current response values with said set of thickness values for one or more measurement points among said plurality of measurement points to produce one or more correlations, said one or more measurement points including said thickness position;
   measuring at least one eddy current response value at said thickness position of said conductive film; and
   determining, using said at least one eddy current responses value and at least one of said one or more correlations, said thickness at said thickness position of said conductive film.

2. The method of claim 1, wherein a sensor position radius among said plurality of sensor position radii and a measurement point among said plurality of measurement points represent the same position on at least one calibration substrate among said set of calibration substrates.

3. The method of claim 1 further comprising determining an offset distance between a sensor position radius among said plurality of sensor position radii and a measurement point among said plurality of measurement points for at least one calibration substrate among said set of calibration substrates.

4. The method of claim 3, wherein said offset distance has a maximum value if said sensor position radius is at an edge of said at least one calibration substrate.

5. The method of claim 1, wherein a difference between a first radius and a second radius of said plurality of sensor position radii is between 1/10 and 1/2 of a transverse size of an eddy current sensor used for measuring said set of eddy current response values.

6. The method of claim 1 further comprising generating a set of calibration curves based on said one or more correlations.

7. The method of claim 1, wherein each calibration curve of said set of calibration curves is created with a mathematical optimization function.

8. The method of claim 7, wherein said mathematical optimization function is an arc tangent function.

9. The method of claim 1 further comprising normalizing said set of eddy current responses values.

10. The method of claim 1, wherein said at least one eddy current responses includes at least one of a voltages value and a current value.

11. The method of claim 1, wherein said substrate is one of a semiconductor wafer and a glass panel.

12. The method of claim 1, wherein said set of eddy current response values are measured by an eddy current sensor located on a sensor swing arm.

13. The method of claim 1, wherein said conductive film is formed of at least one of aluminum, copper, tantalum, ruthenium, tungsten, and platinum.

14. An apparatus for determining a thickness at a thickness position of a conductive film on a substrate, the apparatus comprising:
   a means for correlating a set of eddy current response values with a set of thickness values for one or more measurement points among a plurality of measurement points to produce one or more correlations, said one or more measurement points including said thickness position; and
   a means for determining said thickness using at least one eddy current response value measured at said thickness position and at least one of said one or more correlations,
   wherein said set of eddy current response values is measured at a plurality of sensor position radii on a set of calibration conductive films on a set of calibration substrates, and
   said set of thickness values is measured, without eddy current measurement, at said plurality of measurement points for said set of calibration conductive films on said set of calibration substrates.

15. The apparatus of claim 14 further comprising a means for determining an offset distance between a sensor position radius among said plurality of sensor position radii and a measurement point among said plurality of measurement points for at least one calibration substrate among said set of calibration substrates.

16. The apparatus of claim 14 further comprising a means for generating a set of calibration curves based on said one or more correlations.

17. The apparatus of claim 16, wherein said set of calibration curves is generated using a mathematical optimization function.

18. The apparatus of claim 14, wherein said set of eddy current response values is normalized.

19. The apparatus of claim 14, wherein said set of eddy current response values is measured by an eddy current sensor is located on a sensor swing arm, and said set of thickness values is measured by at least one of a four point probe, a laser acoustic device, a scanning electron microscope, and a transmission electron microscope.

20. The apparatus of claim 14, wherein said conductive film is formed of at least one of aluminum, copper, tantalum, ruthenium, tungsten, and platinum.

* * * * *